(12) United States Patent
Sabczynski et al.

(10) Patent No.: US 10,765,308 B2
(45) Date of Patent: Sep. 8, 2020

(54) METHOD AND APPARATUS FOR TRACKING IN A MEDICAL PROCEDURE

(71) Applicant: Koninklijke Philips N.V., Eindhoven (NL)

(72) Inventors: Joerg Sabczynski, Norderstedt (DE); Heinrich Schulz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 933 days.

(21) Appl. No.: 15/287,896

(22) Filed: Oct. 7, 2016

(65) Prior Publication Data

US 2017/0020376 A1 Jan. 26, 2017

Related U.S. Application Data

(62) Division of application No. 13/378,175, filed as application No. PCT/IB2010/052176 on May 17, 2010, now abandoned.

(Continued)

(51) Int. Cl.
*A61B 1/05* (2006.01)
*A61B 34/20* (2016.01)
(Continued)

(52) U.S. Cl.
CPC .................. *A61B 1/05* (2013.01); *A61B 5/06* (2013.01); *A61B 5/067* (2013.01); *A61B 6/5247* (2013.01);
(Continued)

(58) Field of Classification Search
None
See application file for complete search history.

(56) References Cited

U.S. PATENT DOCUMENTS 7,174,202 B2    2/2007   Bladen et al.
7,233,820 B2 *  6/2007   Gilboa ............... A61B 1/00154
                                                600/407
(Continued)

FOREIGN PATENT DOCUMENTS

DE    102007021717    10/2008
JP      2002263057 A   9/2002
(Continued)

OTHER PUBLICATIONS

Translation of Japanese Office action:Japanese Patent Application No. 2012-516885, Drafting Date: Sep. 30, 2013, Patent Office Examiner: Akiharu Itoh, 4077 2Q00, dated Oct. 8, 2013.

*Primary Examiner* — Katherine L Fernandez
(74) *Attorney, Agent, or Firm* — Sherry Austin

(57) ABSTRACT

A tracking system for a target anatomy of a patient can include a medical device having a body (281) having a distal end (290) and at least one channel (292) formed therein, where the body is adapted for insertion through an anatomy (105) to reach a target area (430); an accelerometer (185) connected to the body and positioned in proximity to the distal end; an imaging device (295) operably coupled with the body; and a light source (297) operably coupled with the body, where the accelerometer is in communication with a remote processor (120) for transmitting acceleration data thereto, where the imaging device is in communication with the remote processor for transmitting real-time images thereto, and where an orientation of the medical device and calibration of direction with respect to the anatomy is determined by the processor based on the acceleration data.

10 Claims, 6 Drawing Sheets

Related U.S. Application Data

(60) Provisional application No. 61/221,138, filed on Jun. 29, 2009.

(51) Int. Cl.
*A61B 6/00* (2006.01)
*A61B 90/00* (2016.01)
*A61B 5/06* (2006.01)
*A61B 1/267* (2006.01)
*A61B 5/055* (2006.01)
*A61B 8/12* (2006.01)
*A61B 5/00* (2006.01)

(52) U.S. Cl.
CPC .............. *A61B 34/20* (2016.02); *A61B 90/36* (2016.02); *A61B 90/37* (2016.02); *A61B 1/2676* (2013.01); *A61B 5/0013* (2013.01); *A61B 5/055* (2013.01); *A61B 6/4441* (2013.01); *A61B 8/12* (2013.01); *A61B 2034/2048* (2016.02); *A61B 2090/364* (2016.02); *A61B 2562/0219* (2013.01)

(56) References Cited

U.S. PATENT DOCUMENTS

| | | |
|---|---|---|
| 8,038,605 B2 | 10/2011 | Tsuji et al. |
| 8,337,397 B2 | 12/2012 | Prisco et al. ................... 600/117 |
| 2005/0020878 A1* | 1/2005 | Ohnishi ................. A61B 1/042 |
| | | 600/117 |
| 2006/0074289 A1* | 4/2006 | Adler ..................... A61B 5/065 |
| | | 600/407 |
| 2005/0522274 | 5/2006 | Russell et al. |
| 2007/0270686 A1* | 11/2007 | Ritter ....................... A61B 5/06 |
| | | 600/424 |
| 2008/0207997 A1 | 8/2008 | Higgins et al. ................ 600/114 |
| 2008/0292046 A1 | 11/2008 | Camus et al. ..................... 378/4 |
| 2009/0149740 A1 | 6/2009 | Hoheisel ........................ 600/424 |
| 2012/0095330 A1 | 4/2012 | Schechter et al. |

FOREIGN PATENT DOCUMENTS

| | | |
|---|---|---|
| JP | 2006230906 A | 9/2006 |
| JP | 2007151862 A | 6/2007 |
| JP | 2007-319622 A | 12/2007 |
| JP | 2009056239 A | 3/2009 |

\* cited by examiner

METHOD AND APPARATUS FOR TRACKING IN A MEDICAL PROCEDURE

CROSS REFERENCE TO RELATED APPLICATION

This application is a divisional of application Ser. No. 13/378,175, filed Dec. 14, 2011. This application claims the benefit of U.S. provisional application Ser. No. 61/221,138, filed Jun. 29, 2009, which is incorporated herein by reference. Related application is Ser. No. 61/221,150, "Method and System for Position Determination," filed Jun. 29, 2009.

The present application relates to the therapeutic arts, in particular to tracking for medical procedures, and will be described with particular reference thereto.

Various techniques and systems have been proposed to improve the accuracy of instrumentality placement (e.g., catheter placement) into the body, such as based on measurements from 3D imaging formats. These imaging formats attempt to locate the entry device in relation to therapy-targeted areas, such as MRI detected target tissue. These imaging formats generate imaging data that are used to determine the appropriate positioning of the device during treatment.

In many cases, the medical device is delivered solely on the basis of this imaging data information, and confirmation of the final position relative to the target may even require a second set of images to be acquired. In some cases where cameras are utilized in the device for visually presenting the path of the device, it is unclear if the correct path is being followed, such as where the device has twisted during movement.

Bronchoscopy is a method to view the interior of the bronchi. A flexible fiber optic device, the bronchoscope, a special kind of endoscope, is introduced through the mouth or nostril of the patient into the airway system. It allows the pulmonologist to see the inside of the trachea, the main bronchi, and the bigger of the small bronchi. Usually, bronchoscopes have a working channel, through which small surgical instruments can be brought to the tip of the bronchoscope.

Lung lesions can be detected on CT scans. In order to come to a reliable diagnosis, a tissue sample must often be investigated. Although it is possible to take the tissue sample with a needle from the outside, this method has certain problems. With the help of a bronchoscope, it is possible to circumvent these problems. Transbronchial endoscopic biopsy of lung lesions is a surgical technique to collect lung tissue via the bronchoscope. A small forceps or biopsy needle is used through the working channel to get lung tissue from behind the bronchial wall.

This Summary is provided to comply with U.S. Rule 37 C.F.R. § 1.73, requiring a summary of the invention briefly indicating the nature and substance of the invention. It is submitted with the understanding that it will not be used to interpret or limit the scope or meaning of the claims.

In accordance with one aspect of the exemplary embodiments, a method of tracking in a medical procedure can include receiving acceleration data from an accelerometer that is integrally connected to a medical device, where the acceleration data is received at a remote processor, and where the medical device is moved through an anatomy of a patient towards a target region; and determining an orientation of the medical device with respect to the anatomy based on the acceleration data.

In accordance with another aspect of the exemplary embodiments, a computer-readable storage medium can include computer-executable code stored therein, where the computer-executable code is configured to cause a computing device, in which the computer-readable storage medium is provided, to: receive orientation data from an orientation sensor that is integrally connected to a medical device, where the orientation data is received at a remote processor, and where the medical device is being moved through an anatomy of a patient towards a target region; determine an orientation of the medical device with respect to the anatomy based on the orientation data; capture real-time images of the anatomy using the medical device; and present the captured images and the orientation of the medical device with respect to the anatomy on a display device operably coupled to the processor.

In accordance with another aspect of the exemplary embodiments, an endoscope is provided that can include a body having a distal end and at least one channel formed therein, where the body is adapted for insertion through an anatomy to reach a target area; an accelerometer connected to the body and positioned in proximity to the distal end; an imaging device operably coupled with the body; and a light source operably coupled with the body, where the accelerometer is in communication with a remote processor for transmitting acceleration data thereto, where the imaging device is in communication with the remote processor for transmitting real-time images thereto, and where an orientation of the medical device with respect to the anatomy is determined by the processor based on the acceleration data.

The exemplary embodiments described herein can have a number of advantages over contemporary systems and processes, including accuracy of surgical device placement and reduction of procedure time by allowing the correct path of the medical device to be more quickly determined. Additionally, the system and method described herein can be utilized through retrofitting existing surgical devices. Still further advantages and benefits will become apparent to those of ordinary skill in the art upon reading and understanding the following detailed description.

The above-described and other features and advantages of the present disclosure will be appreciated and understood by those skilled in the art from the following detailed description, drawings, and appended claims.

The exemplary embodiments of the present disclosure are described with respect to a tracking system for a bronchoscope to be utilized during a procedure for a human. It should be understood by one of ordinary skill in the art that the exemplary embodiments of the present disclosure can be applied to, and utilized with, various types of medical or surgical devices (including other endoscopes or catheters), various types of procedures, and various portions of the body, whether human or animal. The exemplary embodiments can also be used for tracking of a surgical device that utilizes other types of imaging in combination with or in place of a camera, such as ultrasound imaging from an ultrasound device positioned in the surgical device that enters the body. The exemplary embodiments are described herein as using accelerometer tracking in combination with imaging. The use of the method and system of the exemplary embodiments of the present disclosure can be adapted for application to other types of tracking in a target anatomy and can utilize other types of orientation sensing sensors including magnetometers.

Figure 1:
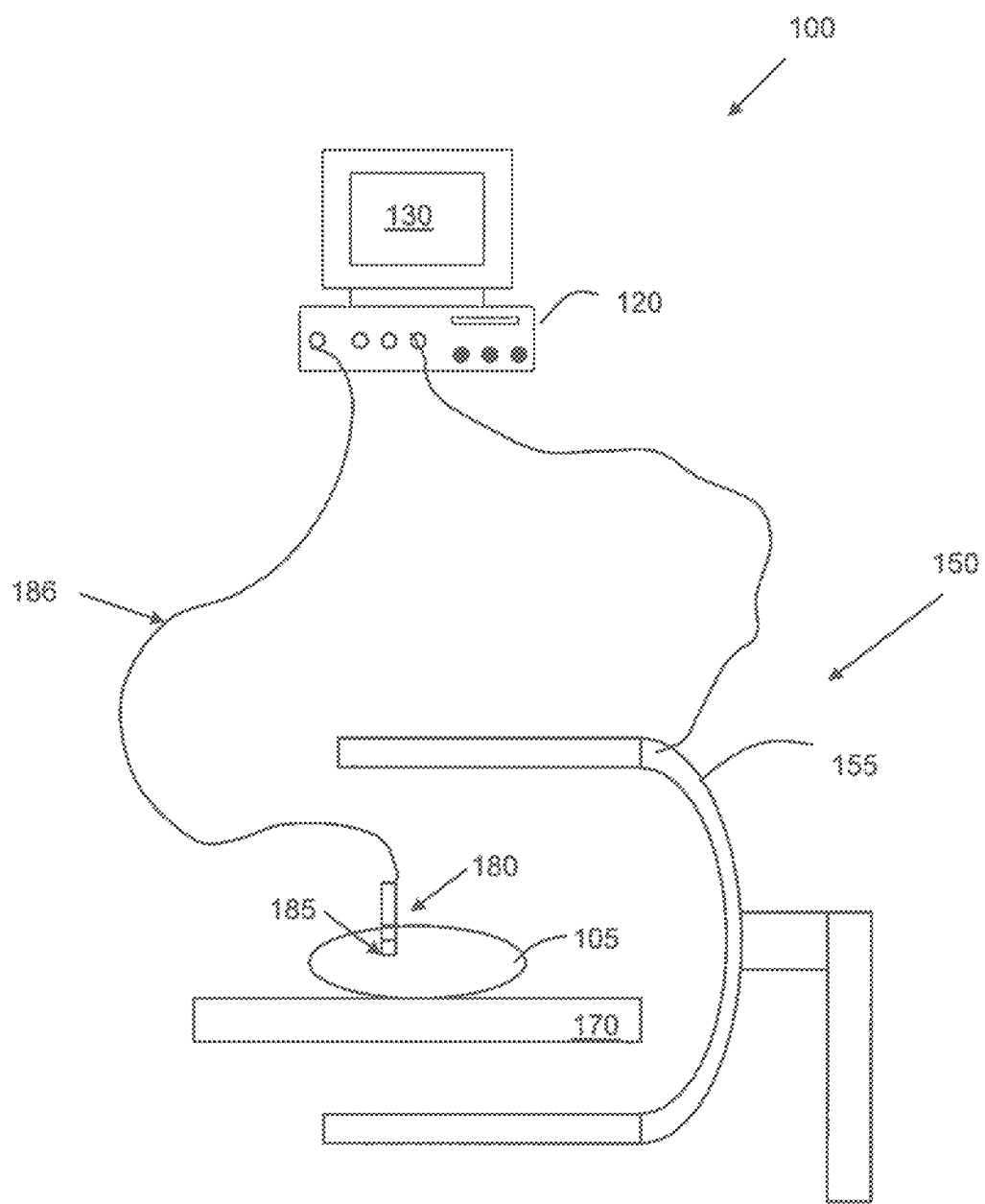
FIG. 1 is a schematic illustration of a tracking system according to one exemplary embodiment for use in a medical procedure.

Referring to FIG. 1, a tracking system 100 is shown which can have a surgical device 180, such as a bronchoscope, with an accelerometer 185 connected thereto. The accelerometer 185 can be positioned along or in proximity to the tip or distal end of the surgical device 180. While the exemplary embodiment shows a single accelerometer 185, the present disclosure contemplates the use of any number of accelerometers that can be in various configurations along the surgical device 180. The surgical device 180 can be utilized in a target anatomy 105 of a patient who can be supported by a support structure 170.

The accelerometer 185 can be a measurement device capable of detecting acceleration of the tip of the surgical device 180 so that orientation information can be generated with respect to a current orientation of the tip. Accelerometer 185 can be of various types including piezoelectric, MEMS, thermal (submicrometre CMOS process), bulk micromachined capacitive, bulk micromachined piezo resistive, capacitive spring mass base, electromechanical servo, null-balance, strain gauge, resonance, magnetic induction, optical, surface acoustic wave, DC response, modally tuned impact, seat pad, PIGA and so forth. In one embodiment, 3-axis accelerometers can be utilized which measure not only the strength of the acceleration, but also its direction.

The accelerometer 185 can be operably connected to a processor 120 that receives the orientation data therefrom. The operable coupling can be through a hardwire, such as line 186, and/or can be a wireless link between the accelerometer 185 and the processor 120. In one embodiment, the orientation data can be raw data, such as a change in voltage, that is measured and transmitted to the processor 120. In another embodiment, the accelerometer 185 can convert the raw data to direction information prior to transmission of the orientation data to the processor 120.

System 100 depicts the orientation data being provided directly to the processor 120. However, the present disclosure contemplates the accelerometer 185 providing the orientation data to a orientation acquisition unit (not shown) which can process the data and then provide it to the processor 120.

In one embodiment, tracking system 100 can be used with, or can include, an imaging modality 150, such as a high resolution imaging modality, including an x-ray scanner 155. For example, a high resolution image of the target anatomy 105 can be generated by the scanner 155 and stored in an image memory. The image memory can be incorporated into processor 120 and/or can be a separate storage and/or processing device. A C-arm x-ray scanning device 155 is shown in FIG. 1 for illustrative purposes, but the present disclosure contemplates the use of various imaging devices, including an open MRI, CT, and so forth. The present disclosure contemplates the use of various imaging modalities, alone or in combination, including MRI, ultrasound, X-ray, CT, and so forth. The present disclosure also contemplates the imaging modality 150 being a separate system that is relied upon for gathering of images, including pre-operative and/or intra-operative images.

Figure 2:
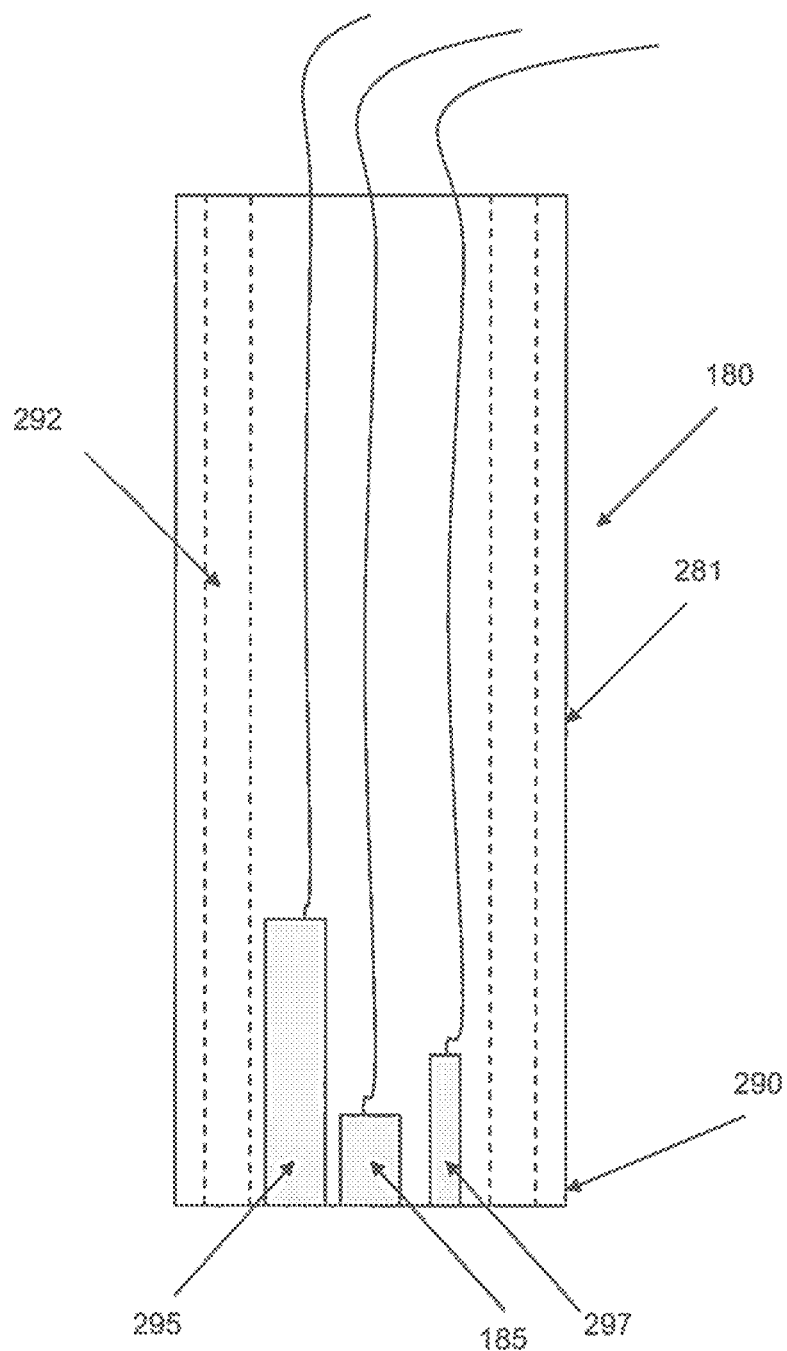
FIG. 2 is a schematic illustration of a surgical device for use with the tracking system of FIG. 1.

Referring additionally to FIG. 2, the surgical device 180 can include one or more channels 292 formed through a body 281 of the device (e.g., a bronchoscope), such as working channels for providing the clinician with access to the target anatomy and suction channels. The body 281 can be made from various flexible materials. The device 180 can include the accelerometer 185 positioned along or in proximity to the tip 290 of the device, including being embedded in a wall of the device or connected to the outside of the device. The device 180 can also include a camera or imaging device 295 and a light source 297. The light source 297 can have a self-contained power source and/or can be connected to an external power source, such as through use of line 186 (in FIG. 1). In one embodiment, the light source 297 can be operably connected to the processor 120 for adjustment of the level of emitted light or other control to be exerted over the light source. In another embodiment, the tip of the surgical device 180 can be provided light by way of fiber optics from an external light generating device.

The camera 295 can be operably connected to a processor 120 that receives the imaging data therefrom. The operable coupling can be through a hardwire, such as the line 186, and/or can be a wireless link between the camera 295 and the processor 120. In one embodiment, the imaging data can be raw data that is captured by the camera 295 and transmitted directly to the processor 120. In another embodiment, the camera 295 can convert the raw data to video information prior to transmission of the imaging to the processor 120. The processor 120 can present the imaging data as a video in real time so that the clinician can see the path that the surgical device 180 is traveling along.

Figure 4:
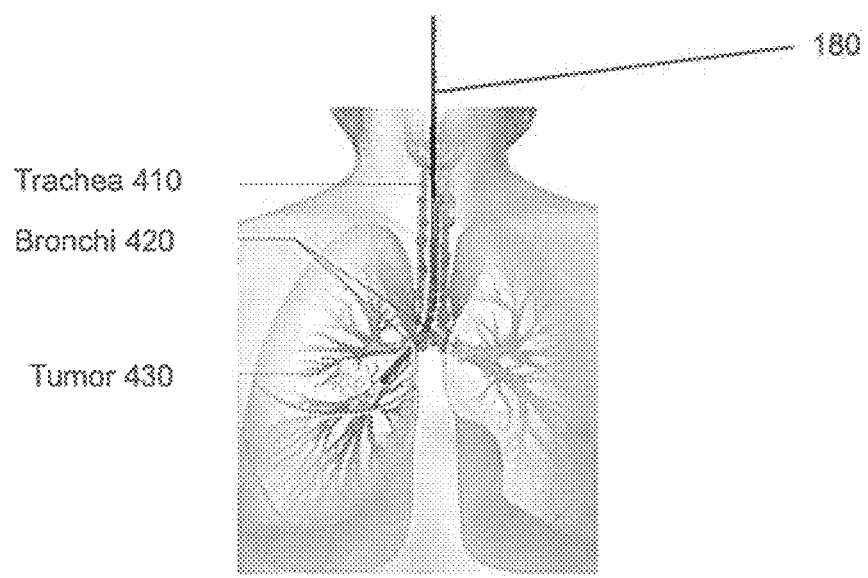
FIG. 4 is a schematic illustration of a patient with a target anatomy.
Figure 5:
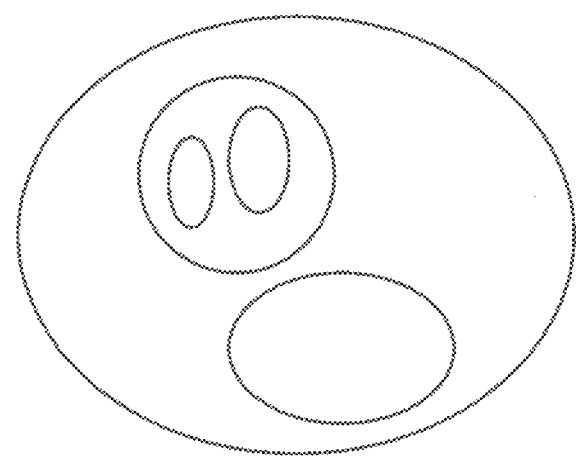
FIG. 5 is an image of a bronchus of a patient captured using the surgical device of FIG. 2 or 3.

Referring additionally to FIGS. 4 and 5, the surgical device 180 can travel down through the trachea 410 and through the bronchi 420 in order to reach a tumor or other target area or region 430. As shown in FIG. 5, the bifurcated structure of the bronchi requires that the clinician select among different paths as the surgical device 180 is being moved during the procedure.

When the surgical device 180 is not moving, the accelerometer 185 measures gravity only. Based on this measurement, it is possible for the processor 120 to determine the up-direction at the tip 290 of the device 180 and relate it to the image (e.g., a CT scan) of the device captured by imaging modality 150. Since it is known how the patient is placed during the procedure, such as a bronchoscopy, it is possible to relate the bronchoscopy image to the CT scan. At a given bifurcation, it is possible to determine which branch to follow in order to reach the target using the acceleration data.

In one embodiment, bifurcations visible in the bronchoscopy image can be detected automatically by means of image processing performed by processor 120. It can be further detected whether the bronchoscope 180 is moved into or out of the bronchi. Together with the information from the accelerometer 185, this combined information can be used to detect the position of the bronchoscope in the bronchial tree. The combination of information from the accelerometer 185 and from image analysis performed by processor 120 facilitates navigation through to the target anatomy.

In another embodiment, a bifurcation indicator can be presented to indicate the orientation of the bronchoscope with respect to the target anatomy. For example, an arrow or the like can be presented that shows which direction is up or which direction is down with respect to a vertical plane. In another embodiment, based on the CT scan, it is possible to render a computer generated view from the position and with the orientation of the actual bronchoscope, so called "Virtual bronchoscopy." This view can be shown side by side with the real image in order to allow for user orientation. In another embodiment, after determining the bifurcation in the video image by image analysis the planned path may be marked, e.g., with a cross.

Figure 3:
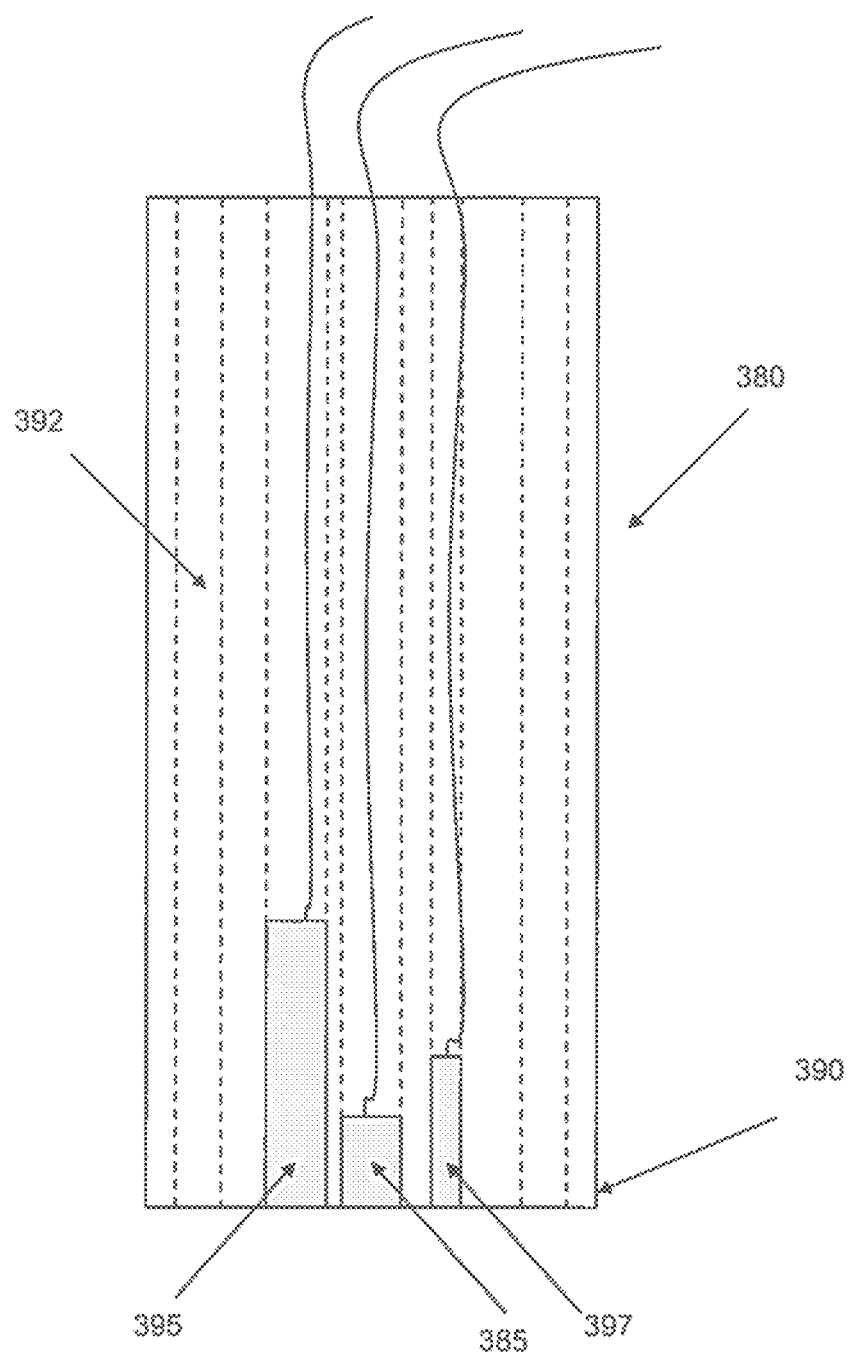
FIG. 3 is a schematic illustration of another surgical device for use with the tracking system of FIG. 1.

Referring additionally to FIG. 3, another surgical device 380 (e.g., a bronchoscope) is shown. Device 380 can include additional channels 392 that allow for positioning one or more of the accelerometer 385, the camera 395 and the light source 397 at or near the tip 390 of the device. These components can be operably coupled to the processor 120 through use of a hardwire and/or wireless link. Once the device 380 reaches its target, one or more of these components can be removed through the channels 392. For example, the accelerometer 385 can be slid through the channel 392 and positioned therein during movement of the device 380. In one embodiment, existing bronchoscopes can be utilized with one or more of the components of device 180. For example, the accelerometer can be positioned into the existing working channel or attached to the tip of the bronchoscope at the outside. In another embodiment, the optical system and lighting components can be fixed in the surgical device 180. Once the target area is reached, the accelerometer 385 can be slid back out through the channel 392 so that the channel can be utilized for other purposes, such as a suction channel or a working channel. In this embodiment, fewer channels may thus be formed through the device 180.

Figure 6:
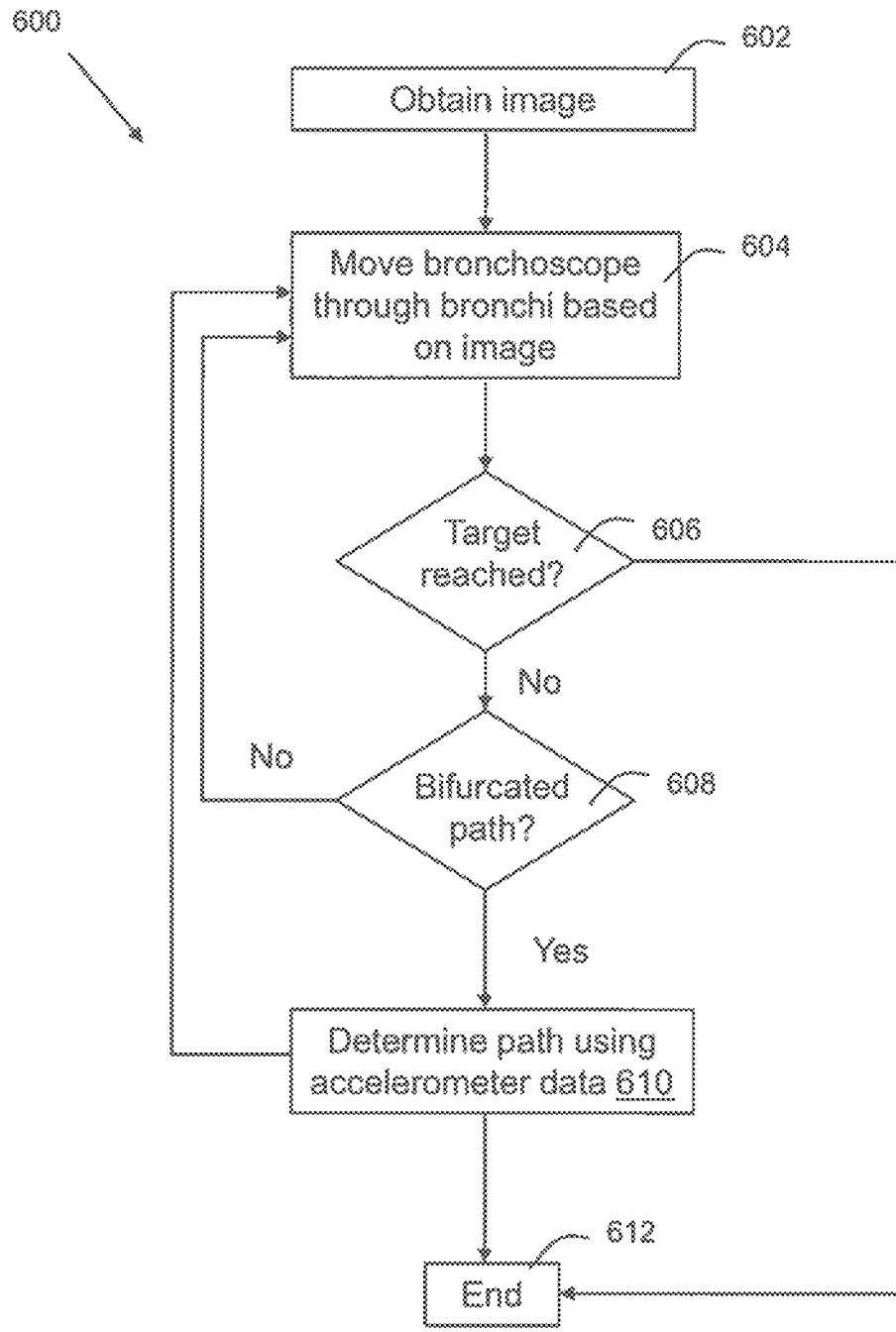
FIG. 6 is a method that can be used by the system and devices of FIGS. 1-3 for performing tracking during a medical procedure.

Referring to FIG. 6, a method 600 of tracking a surgical device, such as a bronchoscope, is shown. In step 602, an image (e.g., a CT image) of the target region, such as the bronchi, is obtained. The image can be a pre-operative image and/or intra-operative image. In step 604, the bronchoscope can be moved through the bronchi where the clinician is viewing the captured real-time video from the camera positioned in the bronchoscope. In step 606, it is determined whether the target has been reached. In step 608, the clinician may come upon a bifurcation in the path. The correct path to proceed along can be determined using the orientation data received from the accelerometer in step 610. These steps can be repeated until the target is reached in step 612. The image can be adjusted so that the position of the bronchoscope and/or the orientation of the bronchoscope is shown therein, such as through using the acceleration data.

System 100 allows the data from the accelerometer 185 to be transferred to the processor 120. In one embodiment, this data can be transmitted along a light guide bundle, which is being utilized for an optical camera operably coupled to the bronchoscope. The processor 120 can receive the orientation data from the accelerometer as well as the bronchoscope image from the video processor for analysis. The processor 120 can analyze and track which bifurcation of the bronchial tree is currently being seen. In one embodiment, the processor 120 can also be connected to the facility network in order to receive the pre-interventional CT scan and the corresponding path planning data. The directional information calculated by the processor 120 can be transferred to the video-processor, where it is combined with the original bronchoscope image data, and then presented on the monitor 130.

Figure 7:
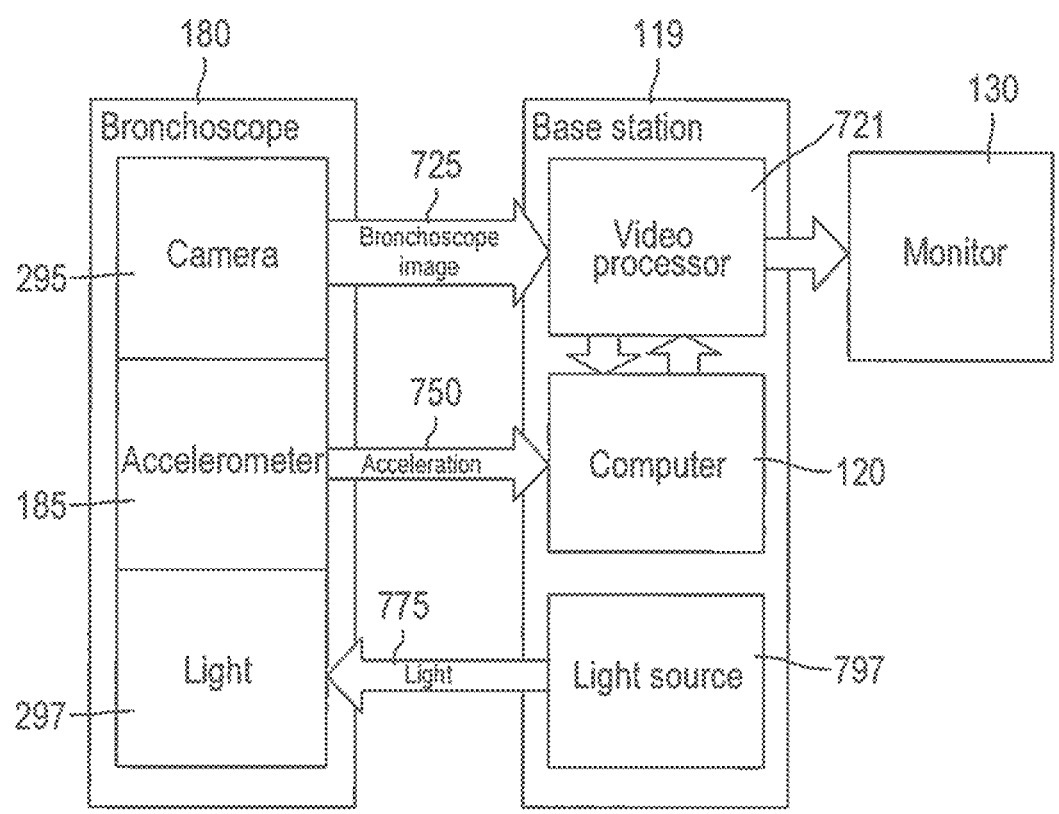
FIG. 7 is a schematic illustration of signal flow between the surgical device and the work station.

Referring additionally to FIG. 7, signal flow between the device 180 and a work or base station 119 is depicted. The signal flow can include acceleration data 750 from the accelerometer 180 to the processor 120; the bronchoscope imaging (e.g., real-time video) 725 from the camera 295 to a video-processor 721; and light 775 from a light source 797 to the light 297 (connected to the bronchoscope).

In one embodiment, the bronchoscope image being presented on the display 130 can be automatically rotated to depict the up-direction based on the orientation data from the accelerometer. In another embodiment, the image processing methods can be used to determine if the bronchoscope is moving in or out of the bronchi. In yet another embodiment, other types of orientation sensors can be utilized for capturing the orientation data. For example, a magnetometer can be used to determine the direction associated with the tip of the bronchoscope and the bifurcated paths based on use of an external magnetic field, including the earth's magnetic field and/or an artificial field. System 100 can be used for bronchoscopic navigation, particularly transbronchial lung biopsies. The system 100 can also be used in other applications, such as a colonoscopy.

In one embodiment, calibration of the direction (iterative refinement of assumed patient position) can be performed where the navigation of the bronchoscope starts with assuming that the patient is in a known position and orientation. The pre-operative CT dataset is thus oriented accordingly to the direction measured by the accelerometer. At the first bifurcation the directions into both bifurcated bronchi are determined with the help of image analysis. These directions are compared to the expected direction based on the accelerometer measurement and the assumed patient orientation and the deviation in orientation is calculated. The assumed patient orientation is corrected by this deviation and for the next bifurcation a better assumption on the patient orientation is used. This procedure can be repeated at the next bifurcation.

A preoperative CT of the lung can be obtained prior to the bronchoscopy. This CT can be analyzed as follows: In the CT image, the position of the lesion of interest, e.g. a lung nodule or tumor, can be determined. This is done manually via clicking in the right slice to the right position. The bronchial tree can be extracted (segmented) from the CT image with the help of suitable image processing methods. The path from the trachea into the bronchial tree to the lesion can be planned. This can be done manually, but automatic methods are also conceivable. Bifurcations along the path can be detected. With this planning step there is enough information available for the intra-operative guidance as describe in the comments above.

Where the bronchi and thus also the bronchoscope tip point directly down or directly up, there may be no usable directional information from the accelerometer. In such a case, it helps to reposition the patient in such a manner, that the bronchoscope tip is pointing into a direction with a horizontal component. Alternatively, the accelerometer can be supported by a magnetometer, which measures the direction of the magnetic field. This is not collinear with the gravitation field except at the magnetic poles.

The invention, including the steps of the methodologies described above, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, including the steps of the methodologies described above, can be embedded in a computer program product. The computer program product can comprise a computer-readable storage medium in which is embedded a computer program comprising computer-executable code for directing a computing device or computer-based system to perform the various procedures, processes and methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with U.S. Rule 37 C.F.R. § 1.72(b), requiring an abstract that will allow the reader to quickly ascertain the nature of the technical disclosure. It is submitted with the understanding that it will not be used to interpret or limit the scope or meaning of the claims.

What is claimed is:

1. A tracking system for use in a medical procedure, comprising
   an endoscope including:
   a body having a distal end and at least one channel formed therein, the body being adapted for insertion through a patient anatomy of a patient to reach a target region;
   an accelerometer connected to the body through the at least one channel and positioned in proximity to the distal end and configure to obtain acceleration data while being moved through the patient anatomy towards the target region;
   an imaging device connected to the body and configured to obtain a real-time image of the patient anatomy; and
   a light source connected to the body; and
   a remote processor configured to receive the acceleration data from the accelerometer, to determine an orientation of the endoscope with respect to the patient anatomy based on the acceleration data;
   to determine a first bifurcation in bifurcated bronchi of the patient anatomy using the real-time image to determine directions at the first bifurcation of the patient anatomy, to compare the determined directions at the first bifurcation with an expected direction into the bifurcated bronchi at the first bifurcation based on the acceleration data from the accelerometer and an assumed patient orientation, to determine a deviation between the determined directions and the expected direction, and to correct the assumed patient orientation by the deviation to generate a first corrected assumed patient orientation.

2. The tracking system of claim 1, wherein the remote processor is further configured to determine directions into bifurcated bronchi of the patient anatomy at a second bifurcation of the patient anatomy, to compare the determined directions at the second bifurcation with an expected direction into the bifurcated bronchi at the second bifurcation based on the acceleration data from the accelerometer and the first corrected assumed patient orientation, to determine another deviation between the determined directions at the second bifurcation and the expected direction at the second bifurcation, and to correct the first corrected assumed patient orientation by the another deviation to generate a subsequent corrected assumed patient orientation.

3. The tracking system of claim 1, wherein the remote processor is further configured to receive at least one of a pre-interventional computed tomography, magnetic resonance imaging or ultrasound scan and corresponding path planning data to the target region.

4. The tracking system of claim 1 further comprising a display operably coupled to the remote processor for displaying directions determined from the first corrected assumed patient orientation.

5. The tracking system of claim 1, wherein the remote processor is further configured to relate the real-time image of the patient anatomy to an image of the endoscope obtained by an external imaging modality.

6. The tracking system of claim 5, further comprising a display operably coupled to the remote processor for simultaneously displaying the real-time image of the patient anatomy and the image of the endoscope.

7. The tracking system of claim 1, wherein the accelerometer is removable from the at least one channel formed in the body of the endoscope, enabling the at least one channel to be utilized as a working channel or a suction channel after reaching the target region.

8. The tracking system of claim 5, wherein the external imaging modality comprises one of MRI, ultrasound, X-ray or CT imaging.

9. The tracking system of claim 5, further comprising a display operably coupled to the remote processor for displaying the real-time image of the patient anatomy, wherein the remote processor is further configured to automatically rotate the real-time image of the patient anatomy to depict an up-direction based on the orientation data from the accelerometer.

10. A tracking system for use in a medical procedure, comprising:
    an endoscope comprising:

a body having a distal end and a plurality of channels formed therein, the body being configured to insert through a patient anatomy of a patient to reach a target region;

an accelerometer in a first channel of the plurality of channels in the body positioned in proximity to the distal end and configured to obtain acceleration data while being moved through the patient anatomy towards the target region; and an imaging device in a second channel of the plurality of channels in the body and configured to obtain real-time images of the patient anatomy; and a processor and a non-transitory memory storing code that, when executed by the processor, causes the processor to perform a process comprising:

receiving the acceleration data from the accelerometer and image data corresponding to the real-time images from the imaging device;

determining an orientation of the endoscope with respect to the patient anatomy based on the acceleration data;

determining a first bifurcation in bifurcated bronchi of the patient anatomy using the image data;

determining a direction at the first bifurcation of the patient anatomy;

comparing the determined direction at the first bifurcation with an expected direction into the bifurcated bronchi at the first bifurcation based on the acceleration data and an assumed patient orientation;

determining a deviation between the determined direction and the expected direction; and correcting the assumed patient orientation by the deviation to generate a first corrected assumed patient orientation.

* * * * *